United States Patent
Vogt et al.

(10) Patent No.: US 9,126,750 B2
(45) Date of Patent: Sep. 8, 2015

(54) DISPENSING DEVICE FOR FLOWABLE MATERIALS

(71) Applicant: Heraeus Medical GmbH, Wehrheim (DE)

(72) Inventors: Sebastian Vogt, Erfurt (DE); Clemens Greiner, Garbsen (DE); Rudolf Hein, Neustadt (DE)

(73) Assignee: Heraeus Medical GmbH, Wehrheim (DE)

( * ) Notice: Subject to any disclaimer, the term of this patent is extended or adjusted under 35 U.S.C. 154(b) by 32 days.

(21) Appl. No.: 14/029,979

(22) Filed: Sep. 18, 2013

(65) Prior Publication Data
US 2014/0076936 A1    Mar. 20, 2014

(30) Foreign Application Priority Data
Sep. 20, 2012 (DE) .......................... 10 2012 018 597

(51) Int. Cl.
*B65D 83/66* (2006.01)
*A61B 17/88* (2006.01)
*B05C 17/015* (2006.01)

(52) U.S. Cl.
CPC ............ *B65D 83/66* (2013.01); *A61B 17/8822* (2013.01); *B05C 17/015* (2013.01)

(58) Field of Classification Search
USPC .................................. 222/389, 386, 325–327
See application file for complete search history.

(56) References Cited

U.S. PATENT DOCUMENTS

| | | | |
|---|---|---|---|
| 1,868,701 A * | 7/1932 | Goerland | 222/263 |
| 1,964,866 A * | 7/1934 | Watson | 220/580 |
| 2,692,706 A * | 10/1954 | Wiksten | 222/326 |
| 2,818,999 A | 1/1958 | Miller | |
| 3,308,990 A | 3/1967 | Klasson et al. | |
| 3,327,906 A * | 6/1967 | Gomann | 222/389 |
| 3,768,472 A * | 10/1973 | Hodosh et al. | 604/143 |
| 3,938,709 A | 2/1976 | Collar | |
| 3,980,209 A * | 9/1976 | Collar | 222/323 |
| 3,983,947 A * | 10/1976 | Wills et al. | 173/169 |
| 4,113,151 A * | 9/1978 | Brown et al. | 222/324 |
| 4,386,717 A * | 6/1983 | Koob | 222/94 |

(Continued)

FOREIGN PATENT DOCUMENTS

| | | |
|---|---|---|
| DE | 102010019224 B3 | 10/2011 |
| DE | 102010019222 A1 | 11/2011 |

(Continued)

OTHER PUBLICATIONS

German Office Action for corresponding DE Application No. 10 2012 018 597.9 dated Apr. 18, 2013.

(Continued)

*Primary Examiner* — Donnell Long
(74) *Attorney, Agent, or Firm* — Norris McLaughlin & Marcus, P.A.

(57) ABSTRACT

A dispensing device dispenses flowable materials from cartridges, whereby the dispensing device comprises a base body, a connecting element for a gas cartridge on the base body, a valve element for controlling a gas flow from the gas cartridge, and a gas-permeable channel connecting the connecting element to the valve element. At least one evaporation container is arranged in the gas-permeable channel such that the gas flow from the gas cartridge is guided through the evaporation container, at least over regions thereof.

20 Claims, 2 Drawing Sheets

(56) References Cited

U.S. PATENT DOCUMENTS

Figure 1:
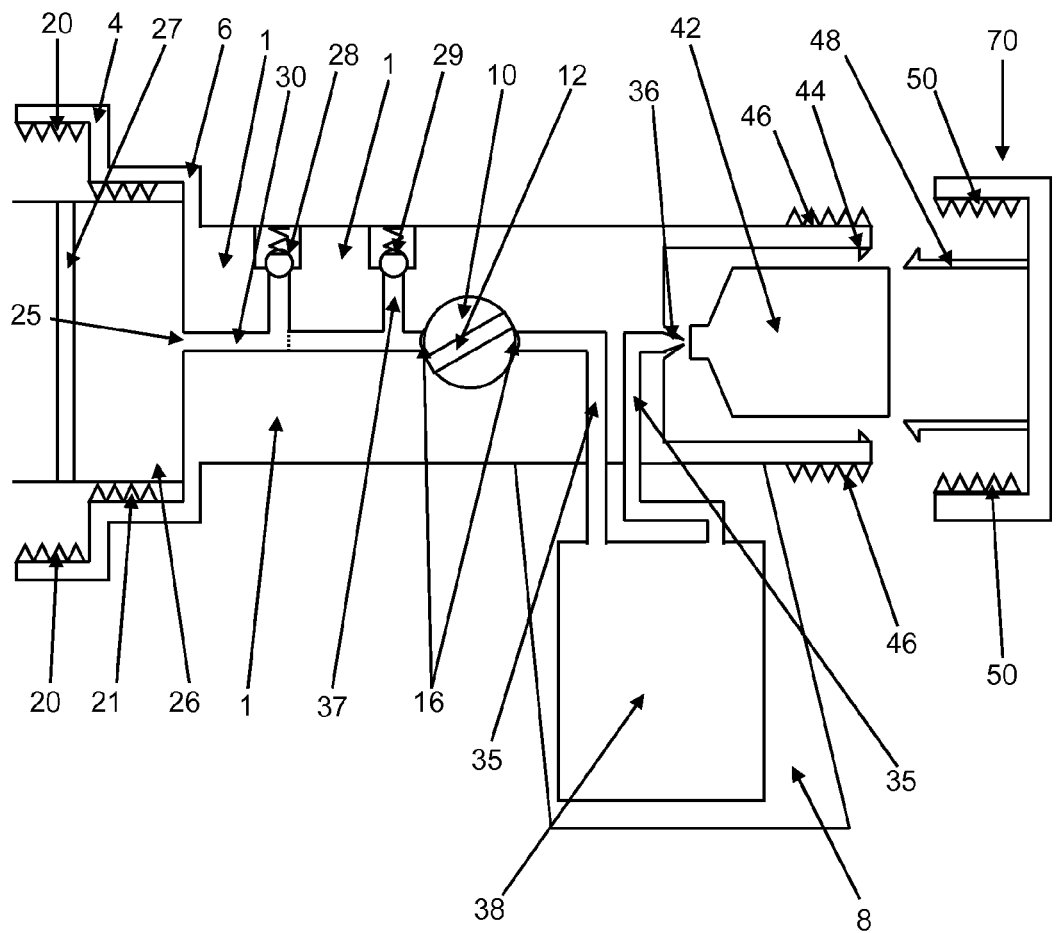

| | | | |
|---|---|---|---|
| 4,441,629 A | 4/1984 | Mackal | |
| 4,925,061 A | 5/1990 | Jeromson, Jr. et al. | |
| 5,181,636 A * | 1/1993 | Anderson et al. | 222/389 |
| 5,514,135 A * | 5/1996 | Earle | 606/93 |
| 6,935,541 B1 | 8/2005 | Campbell et al. | |
| 7,163,130 B2 * | 1/2007 | Lafond | 222/326 |
| 7,185,792 B2 * | 3/2007 | Gibbons et al. | 222/387 |
| 7,188,753 B2 * | 3/2007 | Campbell | 222/389 |
| 7,275,663 B2 * | 10/2007 | Campbell et al. | 222/389 |
| 2004/0074927 A1 | 4/2004 | Lafond | |
| 2005/0230433 A1 | 10/2005 | Campbell | |
| 2005/0247740 A1 | 11/2005 | Puzio | |
| 2008/0142552 A1 * | 6/2008 | Hemsen et al. | 222/334 |
| 2011/0272437 A1 | 11/2011 | Vogt et al. | |
| 2011/0272438 A1 | 11/2011 | Vogt et al. | |

FOREIGN PATENT DOCUMENTS

| | | | |
|---|---|---|---|
| EP | 0014078 | A1 | 8/1980 |
| EP | 0169533 | A2 | 1/1986 |
| EP | 1118313 | A1 | 7/2001 |
| EP | 2384871 | A1 | 11/2011 |
| FR | 1563664 | A | 4/1969 |
| GB | 2162902 | A | 2/1986 |
| JP | S6288899 | A | 4/1987 |
| WO | 9501809 | A1 | 1/1995 |
| WO | 2008109439 | A1 | 9/2008 |

OTHER PUBLICATIONS

European Examination Report for corresponding EP Application No. 13181168.9 dated Jan. 27, 2014.

Japanese Office Action for corresponding Japanese Application No. 2013-194862 dated Nov. 4, 2014.

Chinese Office Action with English-Language translation for corresponding Chinese Application No. 201310426991.5 dated Apr. 23, 2015.

* cited by examiner

DISPENSING DEVICE FOR FLOWABLE MATERIALS

The subject matter of the invention is a dispensing device for expelling flowable materials from cartridges. The dispensing device is intended, in particular, for the dispensing of polymethylmethacrylate bone cements.

PMMA bone cements are in frequent use for mechanical fixation of articular endoprostheses in orthopaedics and accident surgery. It is known to expel from cartridges through the use of compressed gases.

As early as in 1954, U.S. Pat. No. 2,818,999 A proposed a sealing gun that contained a gas cartridge in the handle. Once the cartridge is opened, the compressed gas of the gas cartridge pushed a plunger within the cartridge in the direction of the cartridge head. The flow of the pasty mass was controlled by a central rod that extended through the cartridge and could close the outlet opening of the cartridge.

U.S. Pat. No. 3,938,709 A (1976) describes a dispensing device in which gas pressure is used to squeeze out a tube that is situated inside the hollow gun body. In this context, the gas flow is attained through a simple pin valve fitted with a spring that can be actuated through a manual lever. A device for discharging the gas was not provided. This means that the gun continues to apply pressure to the material due to the existing residual pressure despite the gas feed being interrupted.

EP 0 169 533 A2 (1985) discloses an injection device for viscous substances. In this device, the process of expelling does not continue after the supply of compressed gas is interrupted, because an injection control valve interrupting the flow of viscous substance is situated at the outlet opening. What is interesting in this context is that the valve element of the trigger grip can be used to control both the supply of gas and, simultaneously, the exit of the viscous substance. The injection control valve closes when no compressed gas is applied.

A similar system is described in U.S. Pat. No. 4,925,061 A. However, in this system the injection control valve is actuated through a rod that is connected to the trigger grip.

A gun for expelling bone cement is disclosed in EP 1 118 313 A1. The propulsion is effected through a gas cartridge in this case also. What is essential is that this very complex system includes a rod that serves the purpose to expel the residual amount of cement contained in the dispensing tube. This elegant technical solution is very well-suited for conventional polymethylmethacrylate bone cements. However, said gun cannot be used for cartridge systems for mixing multiple components with a static mixer. Moreover, the manufacture of said gun is very elaborate.

US 2004/0074927 A1 describes an rotary valve body gun which discloses essentially the same features as U.S. Pat. No. 4,925,061 A, and printed specifications US 2005/0230433 A1, US 2005/0247740 A1 and U.S. Pat. No. 6,935,541 B1 basically propose the same technical solution that is known already from EP 0 169 533 A2.

WO 2008/109439 A1 discloses a compressed gas-operated dispensing device that uses a hydraulic medium onto which the compressed gas applies pressure.

It should be noted that the dispensing devices known to date, which are propelled by gas cartridges and have a complex mechanical structure, are suitable for manufacture as single-use articles only to a limited extent or not at all. Moreover, the proposed technical solutions are difficult to implement in the form of plastic injection moulding parts.

In modern vacuum mixing systems, the cement is produced inside a cartridge through mixing the polymer powder with the monomer liquid. The cement dough thus produced is subsequently expelled from the cartridge and applied by means of a hand-operated rotary valve body device. The manual rotary valve body process is experienced as being unpleasant by many users because of the manual force it requires. For this reason, DE 10 2010 019 222 A1 and DE 10 2010 019 224 B3, both applying to the present technical field, proposed pressurised gas-driven expelling devices. Said devices are preferably made from inexpensive plastic material and designed for single use only. A rotary valve in said devices was proposed generally. Said devices utilise pressurised gas as a propellant that is taken from pressurised gas cartridges that are present inside the devices. Pressurised gas can be used to directly apply pressure to feed plungers of cement cartridges and to move them for the rotary valve body process. It is particularly advantageous in this context to use pressurised gas cartridges containing carbon dioxide, which is present as liquid gas in the gas cartridges. It has been shown that said dispensing devices can be used to dispense pasty materials by means of the evaporating carbon dioxide. The pressure of approx. 55 bar produced at room temperature through the evaporating carbon dioxide is sufficient to expel highly viscous bone cements, such as Palacos® R+G, from cartridges.

However, it is disadvantageous that the liquid carbon dioxide in the dispensing device occasionally evaporates incompletely and liquid carbon dioxide advances to the feed plunger. Due to the uncontrolled late evaporation in the space between the feed plunger and the valve element, this produces pressure peaks that lead to undesired short-term accelerations of the feed plunger. This interferes with the precise control of the dispensing process.

Accordingly, it is the object of the invention to overcome the disadvantages of the prior art. The invention is based on the object to develop a dispensing device for flowable materials that is as simple as possible in design and easy to handle. Said device is to use liquid carbon dioxide or any other easily evaporating liquid gas and yet enable precise control of the dispensing process of flowable materials. The term, flowable materials, shall be understood to mean liquid, viscous, even highly viscous, tenacious materials which flow only when pressure is applied to them. The dispensation of the flowable materials is to be effected through compressed liquefied gas, in particular through carbon dioxide, taken from a gas cartridge that is situated in or can be connected to the device. In as far as carbon dioxide cartridges are used, the gas cartridge contains the carbon dioxide as a liquid. The device is to consist of the smallest number of parts possible that can be made through inexpensive injection moulding using conventional plastic materials. It is also desirable for the dispensing device to be suitable as a disposable article for single use.

The object of the invention was therefore met through a dispensing device for dispensing flowable materials from cartridges, whereby the dispensing device comprises a base body, a connecting element for a gas cartridge on the base body, a valve element for controlling a gas flow from the gas cartridge, and a gas-permeable channel connecting the connecting element to the valve element, whereby at least one evaporation container is arranged in the gas-permeable channel such that the gas flow from the gas cartridge is guided through the evaporation container, at least over regions thereof.

In this context, the invention can provide the evaporation container to have a larger cross-section than the gas-permeable channel, preferably a cross-section at least twice as large, particularly preferably a cross-section at least ten times as large.

Moreover, the invention can provide the evaporation container to comprise a volume that is at least half of the volume, preferably is at least equal to the volume of a liquid pressurised gas in the gas cartridge that is intended to be connected to the connecting element or is connected to the connecting element.

Said design variants ensure that liquid components of the gas flow have sufficient space in the evaporation container to separate from the gas flow and transition into the gaseous state.

A refinement of the present invention provides the gas-permeable channel to comprise two connecting elements that are connected to the evaporation container such that the gas flow from the gas cartridge flowing through the evaporation container flows between the connecting elements.

This allows the evaporation container to be replaced or fitted-in subsequently and to thus be adapted to the system, in particular to the volume of the gas cartridge. But even if the connecting elements are connected to the evaporation container fixed in place and in non-detachable manner, there is a resulting advantage in that a stable connection and inexpensive manufacture of the dispensing device according to the invention are enabled.

In this context, the invention can provide the connecting elements not to be attached to the evaporation container on opposite walls of the evaporation container, whereby it is preferred for the connecting elements to be connected to the evaporation container on the same side.

This measure ensures that the liquid components of the gas flow do not simply move straight through the gas-permeable channel due to their inertia and thus get to the valve element or beyond. The more extensive the redirection of the gas flow in the evaporation container and the better gravity can be utilised for separation, the more effective is the separation of the gas flow from the liquid components. For the same reason, the invention can provide the gas-permeable channel to be tortuous, in particular to comprise two changes of direction.

Moreover, the invention can provide a gas-impermeable wall to be arranged in the base body between the connecting elements.

The purpose of the wall also is to ensure that a separation of the gas flow from the liquid components is as efficient as possible. In addition, it ensures that the liquid pressurised gas cannot directly get from the first connecting element to the second connecting element. The liquid pressurised gas is forced into the evaporation container.

A particularly preferred embodiment of the invention can provide, for a normal and intended use of the dispensing device for dispensing a flowable material from a cartridge, the evaporation container to be arranged in the dispensing device in appropriate manner such that the two openings of the gas-permeable channel into the evaporation container are not connected on the floor-side to the evaporation container such that liquid components of the gas flow accumulate on the floor-side in the evaporation container, whereby the openings of the gas-permeable channel into the evaporation container are preferably arranged in the upper region of the evaporation container, particularly preferably in the ceiling wall of the evaporation container.

This arrangement allows gravity to be utilised for separating the liquid components from the gas flow. Moreover, the liquid components are thus prevented from flowing through the gas-permeable channel in the direction of the rotary valve.

Moreover, the invention can provide the dispensing device to comprise a handle, whereby the evaporation container is arranged in the handle, at least over regions thereof, whereby the evaporation container preferably is essentially arranged in the handle and particularly preferably the evaporation container is arranged in the handle.

Said accommodation of the evaporation container or a part thereof ensures that the dispensing device is always held such that gravity can effectively separate the liquid components from the gas flow. Moreover, the handle simplifies the operability of the dispensing device.

In order to provide a dispensing device that is as complete as possible, the invention can provide the dispensing device to contain a gas cartridge, preferably a pressurised gas cartridge, in particular a gas cartridge filled with liquid carbon dioxide.

According to a refinement, the invention can provide a sealing element for connecting the gas cartridge on the connecting element.

The sealing element can prevent inadvertent loss of flowing gas at the connection site.

The invention can further provide, on the base body, an adapter unit for connection of cartridges, whereby a second and a third gas-permeable channel connecting the valve element to the exterior of the adapter unit are provided in the base body.

This design allows different cartridges to be connected to the dispensing device. Moreover, the additional gas-permeable channels increase the ease of use of the dispensing device.

In this context, the invention can provide at least one overpressure valve and/or at least one sterile filter to be connected, or are connectible via the valve element, to the third channel and the overpressure valve and/or the sterile filter to be connected via an opening in the base body to the ambient atmosphere, whereby the opening is not arranged in the adapter unit.

Overpressure valves and sterile filters contribute to the safety during the operation and application of dispensing devices according to the invention.

Preferred dispensing devices can provide the valve element to comprise a first gas channel for controlling the pressurised gas flow and, preferably, an additional second gas channel that is arranged appropriately such that, upon actuation of the valve element, the first gas channel is interrupted and the second gas channel is opened such that the second gas channel is connected via the base body to the ambient atmosphere in a gas-permeable manner.

These measures improve the ease of use of the dispensing device.

The invention can just as well provide the evaporation container and/or the base body to consist of plastic material, preferably of polyethylene.

Moreover, the invention can provide that more than 90% of the dispensing device consists of plastic material, preferably of polyethylene, polyoxymethylene, polyamide or Teflon. The evaporation container can be produced in economically reasonable manner by means of blow moulding. Besides, it can just as well be manufactured by means of injection moulding.

This allows a particularly inexpensive production of the dispensing device to be implemented.

The scope of the invention also includes all other conceivable materials that are suitable for producing pressure-resistant evaporation containers. Accordingly, evaporation containers can also be produced from metal, and in this context, preferably from aluminium or aluminium alloys.

An advantageous refinement of dispensing devices according to the invention consists of at least one overpressure valve (safety pressure relief valve), if applicable, being connected to at least one gas-permeable channel that connects the exterior of the cartridge connector to the valve element in gas-permeable manner, whereby the overpressure valve is connected to the atmosphere surrounding the exterior of the base body in a gas-permeable manner. The overpressure valve can, for example, be designed as a simple ball-type overpressure valve. Said valve opens only from a previously defined internal pressure. The overpressure valve serves to ensure the safety of the dispensing device from bursting in response to excessive pressure by blowing-out the excessive gas into the surrounding atmosphere.

In this context, it has proven to be particularly advantageous to have two overpressure valves in sequence be connected to the gas-permeable channel or, particularly preferably, to the second gas-permeable channel such that the safety of the device from bursting is ensured through the function of the second overpressure valve even in the very unlikely case of failure of one overpressure valve.

Another advantageous refinement of the invention consists of the valve element having a first gas channel for controlling the pressurised gas flow and a second gas channel that is arranged appropriately such that, upon actuation of the valve element, the second gas channel is opened along with the first gas channel being interrupted, whereby the second gas channel is connected to a third gas channel that is arranged in the valve element and is connected to the ambient atmosphere in a gas-permeable manner. This means, that, after the first gas channel is closed, the pressurised gas downstream of the valve element is blown out through the second gas channel and third gas channel into the ambient atmosphere. As a result, the application of pressure to the feed plunger of the cartridge is terminated instantaneously and any after-flow of cement dough is prevented. Moreover, this increases the handling safety of the dispensing device considerably.

The objects of the invention are also met by the use of a dispensing device according to the invention for expelling a flowable material from a cartridge, in which an evaporating liquid gas from a gas cartridge is guided into the evaporation container and the evaporated gas is guided from the evaporation container via a controllable valve element to a feed plunger of the cartridge, whereby the gas pressure propels the feed plunger and the flowable material is expelled from the cartridge by means of the advancement of the feed plunger.

The invention is based on the surprising finding according to which arranging an evaporation container in the path of the gas flow between the gas cartridge and the valve element allows the gas flow to be controlled without any difficulty and continuously through actuation of a valve element, because liquid pressurised gas exiting from the gas cartridge is being evaporated in the evaporation container and therefore upstream of the valve element. This prevents the passage of liquid pressurised gas through the valve element. Accordingly, there is no late evaporation of liquid pressurised gas in the space between the feed plunger and the valve element which allows undesired pressure peaks to be prevented. Moreover, inadvertent propulsion of the feed plunger in the cartridge while the valve element is closed can thus also be prevented according to the invention.

It is also advantageous that the prevention of pressure peaks reduces the pressure load acting on the dispensing device and thus the danger of the dispensing device or parts thereof bursting. Another advantage is that, upon concurrent use of overpressure valves (safety pressure relief valves) in the dispensing device, clearly less pressurised gas is blown out through the overpressure valves than in a dispensing device lacking an evaporation container, which is due to the absence of pressure peaks. As a result, more pressurised gas is available for dispensing the flowable materials. This allows smaller gas cartridges with a smaller filling quantity of liquid pressurised gas to be used.

A dispensing device according to the invention can be made up, for example, as follows from
a) a plastic body;
b) a connecting element for a gas cartridge on the plastic body;
c) a gas cartridge containing liquid gas;
d) a sealing element for a gas cartridge in the connecting element of the gas cartridge;
e) opening means for a gas cartridge in the connecting element;
f) a gas-permeable channel leading from the connecting element of the gas cartridge to a connecting element 1;
g) a gas-permeable channel leading from the connecting element 2 to the valve element;
h) a valve element;
i) an adapter unit on the plastic body for connecting cartridges;
j) at least two gas-permeable channels connecting the exterior of the adapter unit to the valve element in a gas-permeable manner;
whereby an evaporation container having at least two openings is arranged in said gas-permeable channels, whereby a first opening is connected to the connecting element in a gas-permeable manner and a second opening is connected to the connecting element in a gas-permeable manner.

Figure 2:
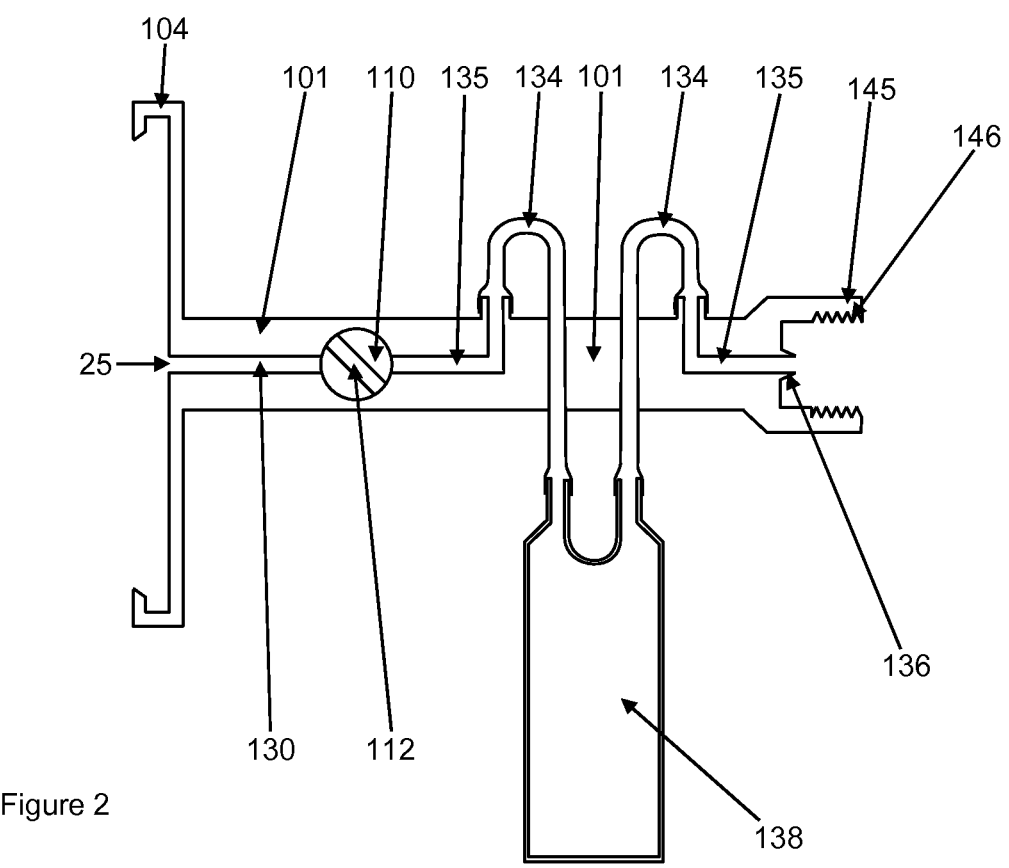

Exemplary embodiments of the invention shall be illustrated in the following on the basis of two schematic figures, though without limiting the scope of the invention. In the figures:

FIG. 1: shows a schematic cross-sectional view of a dispensing device according to the invention; and FIG. 2: shows a schematic cross-sectional view of another dispensing device according to the invention in the absence of a cartridge and of a gas cartridge.

FIG. 1 shows a schematic cross-sectional view of a dispensing device according to the invention having a base body 1 that has a first cartridge connector 4 having a large diameter for cartridges with a large diameter and a second cartridge connector 6 having a smaller diameter for cartridges with a smaller diameter arranged on its front side. The internal cylinder walls of the cartridge connector parts 4, 6 have fixation devices 20, 21 in the form of internal threads provided on them for fixing in place cartridges with external threads (not shown). The fixation devices 20, 21 can just as well be implemented through threads, thread sections or pegs for locking the cartridges in the cartridge connectors 4, 6.

A pistol handle 8 is arranged on the underside, or floor side, of the dispensing device and can be used to hold the dispensing device by one hand. In this context, the underside, or the floor side, of the dispensing device is the side of the dispensing device that faces the floor, i.e. faces downwards, upon normal and intended use of the dispensing device for dispensing a flowable material from a cartridge. The arrangement of the pistol handle 8 shows the floor-ward direction clearly.

Two openings 25 that open into two gas-permeable channels 30 on the front in the base body 1 are situated in the rear wall of the second, inner cartridge connector 6. The gas-permeable channels 30 on the front are arranged behind each other in the image plane according to FIG. 1. The gas-permeable channel 30 on the front extends to a valve element 10 that is provided as rotary valve with a cylindrical valve seat. The front channel is connected with an overpressure valve 29 in the form of a T piece. The gas-permeable channel 30 on the rear, which is not actually situated in the sectional plane, but is drawn here for purposes of illustrating the overall design of the dispensing device, is kinked in upward direction (indicated through the dotted line in FIG. 1) and opens via a second overpressure valve 28 towards the outside into the surroundings, i.e. into the ambient atmosphere of the dispensing device. The connections connecting the gas-permeable channels 30 on the front to the surroundings can have sterile filters (not shown) arranged in them in order to ensure that the interior of the dispensing device cannot get contaminated.

A cartridge 26 is fixed in place in the cartridge connector 6 having the smaller diameter and closes tightly against the cartridge connector 6. This ensures that a gas pressure that is directed through one of the openings 25 onto the floor of the fixed cartridge 26 can also act on a feed plunger 27 of the cartridge 26 arranged on the side of the cartridge floor and does not leak between the cartridge 26 and the cartridge connector 6. For this purpose, sealing elements (not shown) can be provided in the cartridge connectors 4, 6 and/or on the cartridges 26, in particular on the cartridge floors. However, it may also be sufficient to provide a sealed fixation device 20, 21 which can be implemented through a thread, for example.

The rotary valve body 10 showing rotationally-symmetrical geometry over regions thereof is situated in a cylindrical opening in the base body 1 and is mounted in the base body 1 such as to be rotatable about its axis of symmetry (perpendicular to the sectional plane shown in FIG. 1). A first gas channel 12 that extends straight through the rotary valve body 10 is situated in the valve element 10. At an offset of 20° with respect to the openings of the gas channel 12 in the cylinder jacket of the rotary valve body 10, there are sealing cams 16 that serve to seal the gas-permeable channel 30 and a gas-permeable channel 35 on the rear in the base body 1 when the rotary valve body 10 is rotated into the closed position shown in FIG. 1.

The rear part of the base body 1 has a gas-permeable channel 35 on the rear arranged in it that opens into an opening in the valve seat towards the rotary valve body 10. The sealing cams 16 allow the openings towards the gas-permeable channels 30, 35 in the valve seat of the rotary valve body 10 to be closed in gas-tight and pressure-tight manner up to a pressure of seventy bar. On the side of the base body 1 that faces the rear side of the dispensing device, the gas-permeable channel 35 on the rear opens into a hollow mandrel 36 that is open on both sides and has a passage.

Providing an additional drain channel (not shown) allows a gas pressure that is applied onto the feed plunger 27 of the connected cartridge 26 in the region of the cartridge connectors 4, 6 to be relieved. For this purpose, a further gas channel (not shown) can be arranged in the rotary valve body 10 and may allow, with the rotary valve body 10 in appropriate position, a third opening adjacent to the openings 25 to be connected to an additional third gas channel (not shown) on the front. Preferably, additional sealing cams (not shown) would be provided for this purpose to close the openings in the valve seat. Two gas channels 12 are arranged in the rotary valve body 10 and are offset along the axis of symmetry of the rotary valve body 10 and, in addition, are twisted with respect to each other about said axis of symmetry. The offset gas channels 12, only one of which is shown in FIG. 1, are arranged in the rotary valve body 10 in appropriate manner and the gas-permeable channels 30, 35 are arranged in the base body 1 in appropriate manner such that, in two positions of the rotary valve body 10 that can be set by rotating the rotary valve body 10 with respect to the base body 1 in the valve seat, a gas-permeable channel 30 on the front is connected to the gas-permeable channel 35 in the rear via the gas channel 12 or the drain channel (not shown), whereby all other gas-permeable channels 30, 35 are closed in pressure-tight manner by means of the sealing cams 16 of the rotary valve body 10. The width of the front opening 25 towards the rotary valve body 10 that opens into the gas-permeable channel 30 on the front can also be sufficient such that each of the gas channels 12 in the rotary valve body 10 can be connected to the gas-permeable channel 30 on the front, which is then the only one of its kind.

A key element (not shown) is arranged on a side of the rotary valve body 10 that projects from the base body 1 and is engaged by an operating element (not shown) with a matching counterpart for rotating the rotary valve 10 in the valve seat of the base body 1.

The mandrel 36 projects into a hollow space in the rear part of the base body 1 that is suitable for accommodating a gas cartridge 42. The gas cartridge 42 is filled with liquid carbon dioxide. The purpose of the mandrel 36 is to open a gas cartridge 42 whose opening side is being pressed onto the mandrel 36. On the rear end of the hollow space, a locking device 44 is arranged on the inside, and fastening means 46 in the form of an external thread is arranged on the exterior of the base body 1. The locking device 44 serves to prevent a closure cap 70, which can be used to close the dispensing device on its rear, from moving inadvertently. For this purpose, the locking device 44 can engage locking hooks 48 that are arranged on the closure cap 70. The purpose of the fastening means 46 is to securely connect the closure cap 70 to the base body 1 and, in the process, to push the gas cartridge 42 onto the mandrel 36, and to thus open it. For this purpose, fastening means 50 are provided on the closure cap 70 in the form of an internal thread.

The gas-permeable channel 35 on the rear has an evaporation container 38 arranged in it that is situated in the pistol handle 8 of the dispensing device. For this purpose, the gas-permeable channel 35 on the rear is kinked downward in two places in the direction of the pistol handle 8 such that the two ends of the gas-permeable channel 35 on the rear pointing downward open into the evaporation container 38 in a cover surface. The carbon dioxide escaping from the gas cartridge 42 is therefore guided through the evaporation container 38 when it passes the gas-permeable channel 35 on the rear. Any other gas that is liquefied under pressure and evaporated to generate the gas flow can be used just as well instead of carbon dioxide.

The evaporation container 38 has a ten-fold larger cross-section than the gas-permeable channel 35 on the rear and a volume that is approximately equal to the volume of the liquid carbon dioxide in a new (not yet opened) gas cartridge 42.

When liquid carbon dioxide exits from the gas cartridge 42, it passes through the gas-permeable channel 35 on the rear into the evaporation container 38 where it accumulates on the floor of the evaporation container 38. The liquid carbon dioxide evaporates in the evaporation container 38 and is then guided through the gas-permeable channel 35 on the rear to the valve element 10. When the valve element 10 is in the open position (not shown in FIG. 1), the fully evaporated carbon dioxide flows through the gas channel 12 in the valve element 10 and then through the connected gas-permeable channel 30 on the front to the floor side of the cartridge 26 in the cartridge connector 6. In this location, the gas pressure of the carbon dioxide applies pressure onto the feed plunger 27 propelling it forward in the cartridge 26 and thus propelling the cartridge content (a flowable material, for example a bone cement) forward and out of the cartridge 26 from where the cartridge content can be applied.

Closing the valve element 10 (position shown in FIG. 1), the pressure applied onto the feed plunger 27 is relieved very quickly and the propulsion of the feed plunger 27 is thus stopped very quickly. Having the evaporation container 38 therefore ensures in an easy and inexpensive manner that no liquid carbon dioxide flows through the gas-permeable channels 30, 35 and through the gas channel 12 to reach the cartridge connector 4, 6 or into the gas-permeable channel 30 on the front and that no liquid carbon dioxide evaporates in bursts, thereby expanding its volume and generating a pressure surge that leads to inadvertent uneven propulsion of the feed plunger 27 and inadvertent blow-out of the gas through the overpressure valves 28, 29.

The cartridge 26 and the gas cartridge 42 can just as well be separate parts that are not an integral part of the dispensing device.

FIG. 2 shows a schematic cross-sectional view of another exemplary embodiment of a dispensing device according to the invention. A cartridge connector 104 for connecting a cartridge having a feed plunger on the floor side is situated on a base body 101 made of polyethylene. A gas-permeable channel 130 on the front (directed towards the cartridge connector 104) is situated in the base body 101 and extends from a valve element 110 to an opening 25 in the cartridge connector 104.

A connector 145 for a gas cartridge is arranged at the end of the dispensing device on the rear, opposite from the cartridge connector 104. The connector 145 has an internal thread 146 provided in it as fastening means into which an external thread on a matching gas cartridge (not shown) can be screwed. A hollow mandrel 136 is provided as connecting element in the connector 145 on the base body 101 and can be used to open the gas cartridge by screwing it into the internal thread 146.

The hollow mandrel 136 is connected to the valve element 110 through two parts of a gas-permeable channel 135 on the rear, two hoses 134, and one evaporation container 138, which form a gas-permeable channel. A gas channel 112 is situated in the valve element 110 and, with the valve element 110 in an appropriate position, connects the connection and/or channel formed by the gas-permeable channel 135 on the rear, the hoses 134, and the evaporation container 138, to the gas-permeable channel 130 on the front in a gas-permeable manner.

Like the evaporation container 38 according to FIG. 1, the evaporation container 138 serves to evaporate liquid components that get into the connection and/or the channel and thus to prevent these liquid components of liquid gas from reaching the cartridge connector 104 or the gas-permeable channel 130 on the front.

The features of the invention disclosed in the preceding description and in the claims, figures, and exemplary embodiments, can be essential for the implementation of the various embodiments of the invention both alone and in any combination.

LIST OF REFERENCE NUMBERS

1, 101 Base body
4 Cartridge connector having a large diameter
6 Cartridge connector having a small diameter
8 Pistol handle
10, 110 Valve element/rotary valve body
12, 112 Gas channel
16 Sealing cam
20, 21 Fixation device
25 Opening in the cartridge connector
26 Cartridge
27 Feed plunger
28, 29 Overpressure valve
30, 35 Gas-permeable channel
36, 136 Hollow mandrel
37 Drain channel
38, 138 Evaporation container
42 Gas cartridge
44 Locking device
46, 146 Fastening means
48 Locking hook
50 Fastening means
70 Closure cap
104 Cartridge connector
134 Hose
130, 135 Gas-impermeable channel
145 Connector

We claim:

1. A dispensing device for dispensing flowable materials from cartridges, wherein the dispensing device comprises:
    a base body;
    a connecting element for a gas cartridge on the base body;
    a valve element for controlling a gas flow from the gas cartridge; and
    a gas-permeable channel connecting the connecting element to the valve element, wherein the gas-permeable channel comprises two openings; and
    at least one evaporation container arranged in the gas-permeable channel such that the gas flow from the gas cartridge is guided through the at least one evaporation container, at least over regions thereof, wherein the two openings of the gas-permeable channel are connected to a ceiling wall of the at least one evaporation container, when the dispensing device is positioned in an upright position.

2. The dispensing device according to claim 1, wherein the at least one evaporation container comprises a volume that is at least half of the volume of a liquid pressurised gas in the gas cartridge that is connectible to the connecting element.

3. The dispensing device according to claim 1, wherein the two openings of the gas-permeable channel are connected to the at least one evaporation container such that the gas flow from the gas cartridge flowing through the at least one evaporation container flows between the two openings.

4. The dispensing device according to claim 3, wherein a gas-impermeable wall is arranged in the base body between the two openings of the gas-permeable channel.

5. The dispensing device according to claim 1, wherein the at least one evaporation container is arranged in the dispensing device such that the two openings of the gas-permeable channel into the at least one evaporation container are connected on an upper region of the at least one evaporation container such that the liquid components of the gas flow accumulate on a floor-side of the evaporation container, wherein the dispensing device is positioned in the upright position.

6. The dispensing device according to claim 1, wherein the dispensing device comprises a handle, wherein the at least one evaporation container is arranged in the handle, at least over regions thereof.

7. The dispensing device according to claim 1, wherein a sealing element for connecting the gas cartridge is provided on the connecting element.

8. The dispensing device according to claim 1, wherein at least one selected from the at least one evaporation container and the base body consist of plastic material.

9. The dispensing device according to claim 8, wherein at least one selected from the at least one evaporation container and the base body consist of polyethylene.

10. The dispensing device according to claim 1, wherein an adapter unit for connection of at least one cartridge is arranged on the base body, wherein at least one selected from a second gas-permeable channel and a third gas-permeable channel connecting the valve element to the exterior of the adapter unit is provided in the base body.

11. The dispensing device according to claim 10, wherein at least one selected from at least one overpressure valve and at least one sterile filter is connectible via the valve element to at least one selected from the second channel and the third channel and the at least one selected from at least one overpressure valve and at least one sterile filter is connectible via an opening in the base body to the ambient atmosphere.

12. The dispensing device according to claim 1, wherein the dispensing device contains a gas cartridge.

13. The dispensing device according to claim 12, wherein the dispensing device contains a pressurized gas cartridge.

14. The dispensing device according to claim 13, wherein the pressurized gas cartridge is a gas cartridge filled with liquid carbon dioxide.

15. The dispensing device according to claim 1, wherein the at least one evaporation container has a larger cross-section than the gas-permeable channel.

16. The dispensing device according to claim 15, wherein the at least one evaporation container has a cross-section at least twice as large as a cross-section of the gas-permeable channel.

17. The dispensing device according to claim 16, wherein the at least one evaporation container has a cross-section at least ten times as large as the cross-section of the gas-permeable channel.

18. A method comprising:
   connecting a cartridge to the dispensing device according to claim 1 for expelling a flowable material from the cartridge, wherein an evaporating liquid gas from a gas cartridge is guided into the evaporation container the evaporated gas is guided from the evaporation container via the valve element to a feed plunger of the cartridge, and liquid components of the gas flow accumulate on a floor-side in the evaporation container, when the dispensing device is positioned in the upright position, and
   propelling, with gas pressure of the evaporated gas, the feed plunger such that the flowable material is expelled from the cartridge by advancement of the feed plunger.

19. A dispensing device for dispensing flowable materials from cartridges, wherein the dispensing device comprises:
   a base body having a total length defined between a first end and a second end of the base body;
   a cartridge connector, for connecting at least one cartridge, provided at the first end of the base body
   a connecting element, for a gas cartridge on the base body, provided at the second end of the base body;
   a valve element, for controlling a gas flow from the gas cartridge, provided between the first and second ends of the base body, wherein the valve element comprises a rotary valve; a gas-permeable channel connecting the connecting element to the valve element, wherein the gas-permeable channel comprises connecting elements; and
   an evaporation container arranged in the gas-permeable channel such that the gas flow from the gas cartridge is guided through the evaporation container, at least over regions thereof, wherein the connecting elements are connected to a same side of the evaporation container that is adjacent to a bottom side of the dispensing device, when the dispensing device is positioned in an upright position.

20. The dispensing device according to claim 19, wherein the evaporation container is arranged in a handle of the dispensing device.

* * * * *